United States Patent
Pavillon et al.

(10) Patent No.: US 10,495,627 B2
(45) Date of Patent: Dec. 3, 2019

(54) APPARATUS AND METHOD FOR EARLY DIAGNOSIS OF CELL DEATH

(71) Applicant: LYNCEE TEC S.A., Lausanne (CH)

(72) Inventors: Nicolas Pavillon, Lausanne (CH); Jonas Kühn, Vevey (CH); Pascal Jourdain, Sergy (FR); Christian Depeursinge, Préverenges (CH); Pierre Julius Magistretti, Epalinges (CH); Pierre Marquet, Cheseaux-sur-Lausanne (CH)

(73) Assignee: LYNCEE TEC S.A., Lausanne (CH)

( * ) Notice: Subject to any disclaimer, the term of this patent is extended or adjusted under 35 U.S.C. 154(b) by 300 days.

(21) Appl. No.: 15/147,763

(22) Filed: May 5, 2016

(65) Prior Publication Data
US 2016/0245787 A1  Aug. 25, 2016

Related U.S. Application Data

(62) Division of application No. 13/816,855, filed as application No. PCT/IB2011/053623 on Aug. 16, 2011, now Pat. No. 9,360,468.

(30) Foreign Application Priority Data

Aug. 20, 2010  (WO) .................. PCT/IB2010/053768

(51) Int. Cl.
*G01N 33/483* (2006.01)
*G01N 21/45* (2006.01)
(Continued)

(52) U.S. Cl.
CPC ....... *G01N 33/4833* (2013.01); *G01N 21/453* (2013.01); *G03H 1/0005* (2013.01);
(Continued)

(58) Field of Classification Search
CPC ............. G01N 33/4833; G01N 21/453; G01N 2021/1789; G01N 2510/00; G03H 1/0866; G03H 1/0005; G03H 2001/005
See application file for complete search history.

(56) References Cited

U.S. PATENT DOCUMENTS 6,262,818 B1 * 7/2001 Cuche .................. G03H 1/0443
                                                    359/10
8,848,199 B2    9/2014 Choi et al.
(Continued)

FOREIGN PATENT DOCUMENTS

WO          2000/20929         4/2000
WO    WO 2009/111609 A2 *  9/2009  ............... G03H 1/08
WO          2012/023105        2/2012

OTHER PUBLICATIONS

Mutsumi et al. "Noninvasive quality estimation of adherent mammalian cells for transplantation" *Biotechnology and Bioprocess Engineering* 15(1):54-60 (Feb. 2010).
(Continued)

*Primary Examiner* — Michael L Hobbs
(74) *Attorney, Agent, or Firm* — Nixon & Vanderhye P.C.

(57) ABSTRACT

An apparatus for measuring through optical means temporally resolved, optical properties, and/or phenotypes, linked to cellular homeostasis. Those temporal measurements enable the detection of cell regulation through various channels linked to homeostasis, in order to assess cell viability or early cell death through rapid diagnostic.

24 Claims, 5 Drawing Sheets

(51) Int. Cl.
*G03H 1/00* (2006.01)
*G03H 1/08* (2006.01)
*G01N 21/17* (2006.01)

(52) U.S. Cl.
CPC ... *G03H 1/0866* (2013.01); *G01N 2021/1789* (2013.01); *G01N 2510/00* (2013.01); *G03H 2001/005* (2013.01)

(56) References Cited

U.S. PATENT DOCUMENTS

| 2005/0036181 A1 | 2/2005 | Marquet et al. |
| 2010/0060897 A1 | 3/2010 | Gustafsson |
| 2013/0210066 A1 | 8/2013 | Pavillon et al. |

OTHER PUBLICATIONS

Pavillon et al. "Cell morphology and intracellular ionic homeostasis explored with a multimodal approach combining epifluorescence and digital holographic microscopy" *Journal of Biophotonics* 3(7):432-436 (Jul. 2010).
Pavillon et al. "Early cell death detection with digital holographic microscopy" *PLoS One* 7(1):e30912 (Jan. 2012).
Int'l Search Report for PCT/IB2011/053623, four pages (dated Jan. 2012).
Written Opinion for PCT/IB2011/053623, eight pages (dated Feb. 2013).
Int'l Preliminary Report on Patentability for PCT/IB2011/053623, seven pages (dated Feb. 2013).

\* cited by examiner (a)

(b)

(c)

(a)

(b)

APPARATUS AND METHOD FOR EARLY DIAGNOSIS OF CELL DEATH

This application is a divisional of application Ser. No. 13/816,855, filed Apr. 10, 2013, now allowed; which is the U.S. national stage of Int'l Application No. PCT/IB2011/53623, filed Aug. 16, 2011; which claims priority benefit of Int'l Application PCT/IB2010/053768, filed Aug. 20, 2010; the entire contents of each of which are hereby incorporated by reference.

FIELD OF INVENTION

The present invention relates to methods and apparatuses for detecting the state (alive or death) of a cell or a group of cells.

BACKGROUND OF THE INVENTION

The detection of cell death is a highly relevant biomarker for many biological processes related to various application fields including the severity/progression of diseases, the efficacy of various therapies and the drug safety evaluation. Cell death can proceed by several distinct pathways, including mainly apoptosis, necrosis and autophagy, which are characterized by a distinct set of temporal, morphological, biochemical, and genetic characteristics. For a detailed description of the various mechanisms involved in the different cell death pathways, see for example Duprez, L. et al. "Major cell death pathways at a glance", *Microbes Infect.* 11(13), 1050-1062 (2009).

Although, in a whole organism, certain types of cell death, including apoptosis, result in the controlled breakdown of the cell avoiding any intracellular release, in vitro, the different cell death pathways proceed to an end-stage called secondary necrosis, which shares many features with primary necrosis pathway, in particular the loss of cell membrane integrity and the subsequent release of the cellular content into the surrounding extracellular space. Consequently, in vitro assays usually differentiate between viable and non viable cells by assessing membrane integrity thanks to inclusion and/or exclusion dyes (trypan blue or propidium iodide, for example) or the detection of specific intracellular compounds in the surrounding medium (lactate deshydrogenase release (LDH)). However, depending on the stimulus having induced cell death, such cell viability essays assess a late stage of the cell death processes with extrinsic contrast agents and usually require several steps (washing, harvesting, solubilization etc.) which take several hours for completion.

On the other hand, as mentioned before, specific morphological and biochemical features (often called "phenotypes") accompany or are linked to cell death processes and are often used to define and recognize the different cell death pathways. For example, the loss of cell volume or cell shrinkage that occurs during apoptosis is a key morphological characteristic separating this physiological cell death process from an accidental one as necrosis, characterized by an initial cell swelling. Originally, the volume regulation is driven by homeostasis, which is the concept of the cell regulating within its environment. On a general point of view, a combination of various parameters and phenotypes linked to the homeostasis, such as protein concentration, ion concentration, water content, etc., can provide useful indicators about the cell viability.

It was indeed shown that loss of the cell normal regulatory capability is considered as a trigger for cell death. For example, cell volume deregulation was shown to be a relevant indicator for cell death triggering, and intracellular ionic concentration deregulation is seen as a primary indicator of cell biological processes dysfunction, as shown for example in Bortner, C. and Cidlowski, J., "The role of apoptotic volume decrease and ionic homeostasis in the activation and repression of apoptosis," *Pflug. Arch. Eur. J. Physiol.* 448(3), 313-318 (2004). However, minor variations of those parameters occur in accordance with the normal cell activity and cells have inherited regulatory mechanisms to compensate for these minor variations in order to maintain in particular appropriate balance of ions across their cell membrane. One can thus identify, for a given regulatory indicator, a variation range which lies in normal life cycle of the cell, and other ranges indicating a lack of regulation capacity of the cell, which can lead to cell death mechanisms triggering.

GENERAL DESCRIPTION OF THE INVENTION

The present invention makes use of the direct relationship that links optical properties to intracellular concentrations (e.g. water content, protein concentration, ions concentrations) and to cellular morphology (e.g. cell volume, cell surface, cell thickness). As a result of these relationships, optical measurements can be used as a direct mean to monitor the regulatory behavior of cells. In other words, the present invention uses temporally resolved measurement of optical properties, in order to define phenotypes enabling to monitor the ability of cells to restore their homeostatic equilibrium after a perturbation of their environment. Such optical monitoring enables non-invasive, possibly early diagnosis of cell death.

The invention more precisely concerns a method and an apparatus as defined in the claims.

The aim of the proposed invention is to provide a method and an apparatus measuring cell regulatory parameters and phenotypic evolution through time, in order to enable a rapid or time-efficient diagnostic of cell viability. Measuring a given regulatory property, such as for example volume, intracellular ionic concentration, intracellular water content, proteins concentrations, morphology, or more generally a combination of phenotypes in a time-resolved manner enables to determine the cell viability with a high sensitivity and temporal resolution, that can usually lead to a rapid and early diagnostic.

The invention describes an apparatus performing the measurement through optical means, so that the regulatory property, or phenotype, or a combination of them, of interest is deduced from the measurement of an electromagnetic wave that interacted with the bio-sample, thus providing a non-invasive measurement. The apparatus comprises a processing unit, which deduces the optical parameter of interest from the measurement of this said electromagnetic wave. The apparatus comprises also an analysis unit providing real-time processing of the measurement, in order to deduce the temporal change of the measured regulatory parameters. From this temporal measurement, a post-processing unit is capable of deducing a diagnostic about cell viability, by processing the time-resolved measurement in order to provide a decision, that can be either implemented in quasi real-time to get fast and early diagnostic, or as a pure data processing step to be performed anytime a-posteriori.

As the measurement is performed globally on the whole sample through optical means, the detection can be employed on single cells individually, on cell cultures as a whole, as well as biological tissues.

As mentioned previously the invention concerns an apparatus and a method for fast and early diagnosis of cell death by time-resolved measurement of an optical parameter, said time-resolved measurement of phenotypes being an indicator of the ability of cells to restore, by spontaneous regulation, their homeostatic equilibrium after a perturbation of their environment. The speed advantage of the approach does not preclude long-duration experiments or a-posteriori data processing depending of the chemical agent, cell type or experimental requirements. If the measurement of the optical parameter indicates a reversible behavior over time, cells are considered as alive. On the contrary, if the measurement of the optical parameter indicates a non-reversible behavior over time, cells are considered as dead. The measured optical parameter can be for example the optical phase, or the optical path length, which are of particular relevance to monitor cellular regulation behaviors, since these parameters are directly related to the refractive index of the cell, an optical property which is highly sensitive to intracellular concentrations of proteins or ions, or water content. In addition, optical phase and optical path length are also highly sensitive to morphological properties (cell thickness, volume, projected area, etc. . . . ) and intra-cellular refractive index (linked to e.g. dry-mass, water content, etc. . . . ). Within the frame of the present invention all these parameters can define phenotypes, that can be either linked to a physical metric (e.g. volume, projected area, intracellular refractive index, . . . ) or to a cell culture behavior over time (e.g. mytosis rate, motility, culture grow patterns, etc. . . . ), to be evaluated and tracked over time, either individually or in combination, to finally get a time-efficient viability diagnostic based on their reversibility.

DETAILED DESCRIPTION OF THE INVENTION

Figure 1:
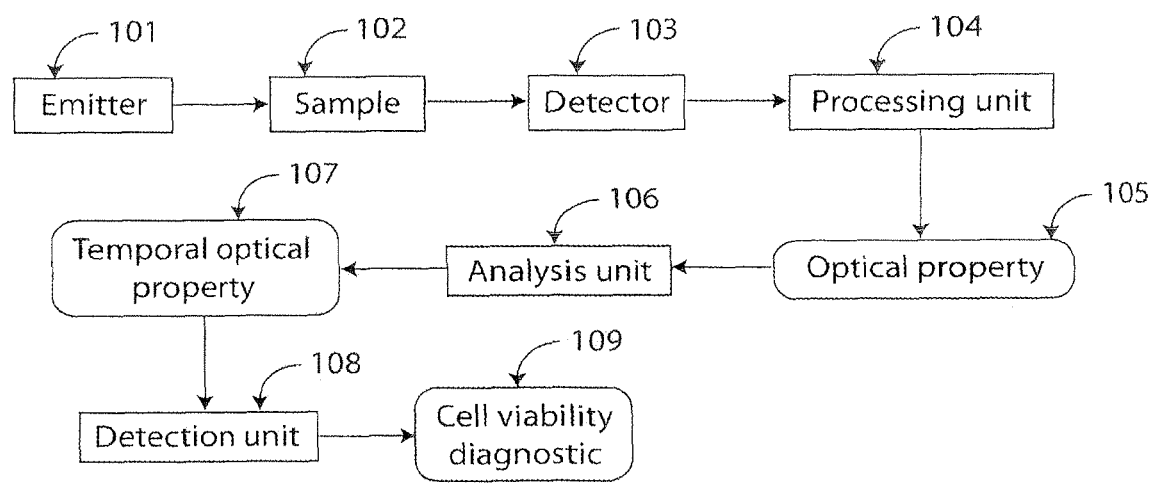
FIG. 1 presents the scheme of an apparatus for measuring, in a time-resolved way, an optical property employed as an indicator of homeostasis on a bio-sample for fast cell death detection.

The basic principle of the described invention relies on a time-resolved measurement of one (or several) optical property(-ies), said time-resolved measurement of phenotypes being used as an indicator of cell viability. More precisely and simply described, the present invention analyses the reversibility, or the non-reversibility, of temporal variations of one, or a combination of, phenotype(s) based on the measurement of an optical property of a biological sample, and provides a diagnosis of cell death on the basis of this analysis, said diagnosis being based on the following considerations:

Reversible variations indicate that a regulation process occurred to restore the homeostatic equilibrium of cells, indicating that the cell can be considered as alive.

Non-reversible variations, whose amplitudes are higher than expected for a standard physiological behavior, are the indicator of cellular death.

Two general principles govern cell death diagnosis according to the present invention:

First a biological principle that links the cell death process to cellular regulation processes: Simply explained, after a perturbation of its environment, e.g. the exposition to a toxic substance, a cell that succeeds to regulate itself to restore a state of equilibrium with respect to its environment (further called homeostatic equilibrium), is a cell that can be considered as a healthy or living cell. On the contrary, a cell that fails in restoring its homeostatic equilibrium can be considered as dead, or at least, his future death can be diagnosed. This first principle explains how an analysis of reversibility/non-reversibility, can be used to diagnose cell death.

Second a physical principle that links the optical properties of a cell to cellular regulation processes: Indeed, among the diverse forms of regulation processes that a cell can use to adapt itself to a perturbation of its environment, several forms of regulation affect for example the cellular morphology (e.g. the cell volume, the projected cell area, etc. . . . ) and/or the intracellular concentrations (e.g. proteins or ions concentrations, water content, dry mass, nucleus/DNA condensation, etc. . . . ). As a consequence, the optical properties of a cell are modified by a regulation process, since optical measurement methods are sensitive to both morphological parameters and intracellular concentrations. For example, changes of intracellular concentrations induce automatically changes of the refractive index of the cell, which modifies the speed of propagation of electromagnetic waves (optical waves in particular) traveling through the cell. This second principle explains how temporally-resolved measurement of an optical property can define various phenotypes that can be used to monitor a cell regulation process, thus enabling a diagnosis of cell death, according to the first principle explained before.

These two principles will be described in more details in what follows, and a concrete implementation of the present invention will be described.

Cells regulate themselves within their environment through homeostasis, depending on the extracellular concentrations of biochemical compounds. For instance, osmosis will induce water movements through the cell membrane, thus inducing changes in ionic concentrations, and volume variations. The proposed apparatus is based on temporal measurement of such parameters, or more generally any phenotype that can be retrieved through optical path length measurement, in order to measure the regulation capabilities of the cellular body. Small variations are considered to be physiologically relevant in a healthy process of the cell life cycle, as it preserves its environment through homeostasis. On the other hand, strong changes which cannot be regulated through standard channels lead to internal deregulation, and ultimately trigger cell death mechanisms, during which a cascade of phenomena occurs. The measurement principle therefore relies on the detection of such deregulations for an early diagnostic of cell viability. The main advantage of this approach is to provide a faster way of detection, as deregulations (biochemical, volume, morphological phenotypes, etc.) are the primary causes for triggering the cell death mechanisms. Detecting such deregulations through their phenotypic signatures makes it thus possible to detect the cause of cell death triggering instead of consequences of cell death, such as cell viability assessments based on extraneous dyes relying on cell permeability, which occur when a specific type of cell death—necrosis—is at its late stages.

One can cite many different changes in the homeostasis of a cell when death pathways are triggered. We give here a description of some of the most typical phenotypes, although this description is not meant to be exhaustive. In the case of apoptosis, which corresponds to the controlled death aiming at recycling cell organelles without releasing intracellular compounds into the surrounding medium, one can cite cell shrinkage, increase of the intracellular ionic or protein concentrations, important and rapid morphological variations of the membrane surface, adenine triphosphate (ATP) depletion, etc. Then, the case of necrosis, which corresponds to the uncontrolled pathological death, is characterized by cell swelling, loss of morphology control leading to spherical shape, dilution of the intracellular content, increase of the cell membrane permeability, etc. Finally, autophagy is a normal process occurring as suppression of organelles inside the cell and selection of intracellular compounds for preservation of the stability of the genome. In the context of cell death, it is characterized by an absence of fragmentation of the nucleus until late stage, strong lysosomic activity and no division of the cell body in several small compartments.

However, in usual cases, the different pathways leading ultimately to cell death are in competition, so that many different variations in regulation occur, and that one parameter only cannot be employed to diagnose a specific type of death. Nevertheless, all those events can be related to changes in homeostasis, and can be employed in a global way for fast detection.

In its most simple implementation, the invention is based on an apparatus employing the elements described below, and shown in FIG. 1. An emitter (101) generates an electromagnetic wave, which passes through the sample (102). After having interacted with the sample, the wave is measured with a detector (103), which sends the measured signal to a processing unit (104). The processing unit converts the measured signal to one, or several, optically-resolved phenotype(s) of interest (105), such as cell volume or intracellular compound concentration, for instance. This phenotype, or a combination of several phenotypes, is/are then stored and processed during time by an analysis unit (106), providing the time-resolved monitoring of the phenotype(s) of interest (107), which can then be processed for analysis by a detection unit (108), which finally provides a diagnostic (109) through analysis of the temporally resolved phenotype(s).

In its practical implementation, the apparatus should include a measurement device to measure a given optical property corresponding to a specific phenotype, and a processing unit to derive and analyze the measured data. Due to the various phenotypes which can be measured to estimate the regulation capability of cells, many different optical means can be developed for this purpose. To estimate for instance the volume of cells, interferometry can be employed through the measurement of the optical path length induced by cells, such as in white light interferometry, holography, or digital holography, or through z-resolved measurements, such as with confocal microscopy, optical coherence microscopy, phase retrieval through z-stack of intensity images (transport-of-intensity), or other scanning or phase retrieval methods, provided that the scanning procedures still enables a temporal monitoring. To estimate for instance ionic or protein content, one could use interferometry or refractometers, where the refractive index is related to the optical path length induced by the cell, or functional imaging such as fluorescence microscopy, where specific fluorophores enable the measurement of specific intracellular compounds. The processing unit can be for instance a computer with dedicated image post-processing software working either on classical central processing units (CPU) or on graphical processing units (GPU) for parallel computing, or a dedicated hardware (such as a PCI board) for direct processing. Typically, either online computation of the temporal data and diagnosis (simultaneous to measurement) or offline (after measurement) could be performed depending on the specific implementation.

Figure 2:
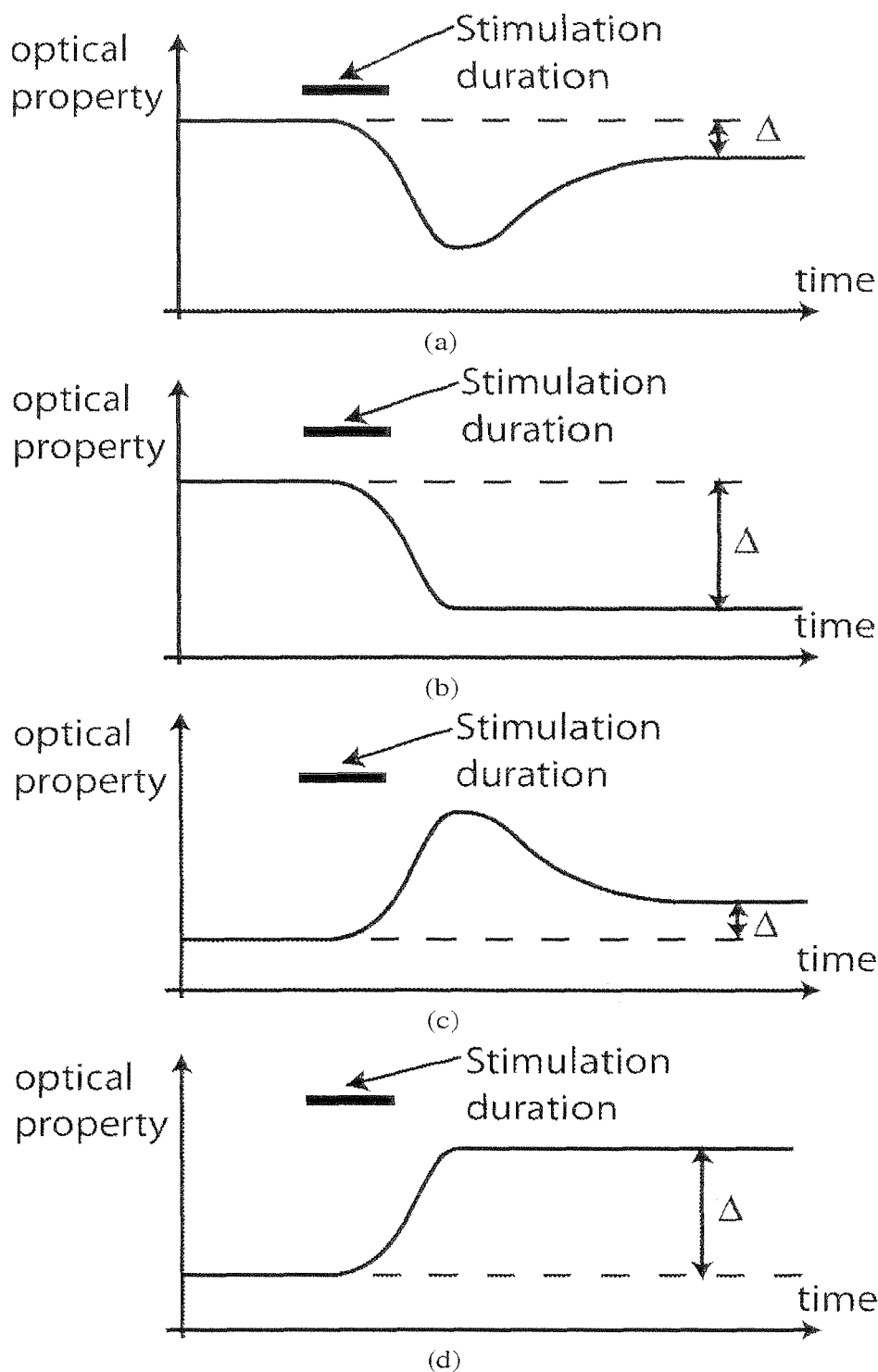
FIG. 2 presents schematically some examples of possible responses from a measurement of an optical property through time on a bio-sample, according to the present invention. (a) The signal drops, but regulation occurs. (b) The signal drops and cannot be compensated through regulation. (c) The signal increases, but regulation occurs. (d) The signal increases and cannot be compensated through regulation.

Typical temporal signals that can be obtained through this apparatus are shown schematically in FIG. 2, for different responses of the bio-sample. In FIG. 2(a-b), the case where the optical property decreases under stimulation (chemical, electrical, etc.) is presented. In FIG. 2(a), the optical property measurement is recovering to a level comparable to before the stimulation, where the difference $\Delta$ can be considered as being within physiological variations, indicating that the cell regulated itself, and can thus be considered as viable. On the other side, in the case of FIG. 2(b), the decrease is not compensated through regulation phenomena, so that no increase after the end of the stimulation is seen, and the difference of the optical property $\Delta$ cannot be considered as being in physiological ranges, so that the cell is not viable. On the other hand, FIG. 2(c-d) presents a similar case, but where the optical property measured on the cell response is increasing through stimulation. In FIG. 2(c), the regulation is occurring and compensating for the changes, showing again the cell viability, while in FIG. 2(d), the regulation is not compensating for the changes, demonstrating that the cell is non-viable.

Depending on the type of processing unit employed, the detection can be applied to various types of bio-samples. Typically, the detection can be applied at a single cell level, but different type of processing can lead to an interpretation of the phenotypes at a more global level, so that direct detection on a cell culture or a biological tissue could be employed in a perspective of statistical treatment, for instance.

Feasibility Demonstration

We present in this part of the document a validation of the detection approach described above. In this particular case, the implementation of the apparatus is an interferometric measurement device based on digital holographic microscopy (DHM), as described for example by E. Cuche and C. Depeursinge in EP1119798—METHOD AND APPARATUS FOR SIMULTANEOUS AMPLITUDE AND QUANTITATIVE PHASE CONTRAST IMAGING BY NUMERICAL RECONSTRUCTION OF DIGITAL HOLOGRAMS (2000), and by T. Colomb et al. in WO2006090320—Wave Front Sensing Method And Apparatus (2006). In EP 1451646—APPARATUS AND METHOD FOR DIGITAL HOLOGRAPHIC IMAGING (2003), P. Marquet et al. present an application of the method in biology that describes quantitative phase-contrast imaging in biology.

Figure 3:
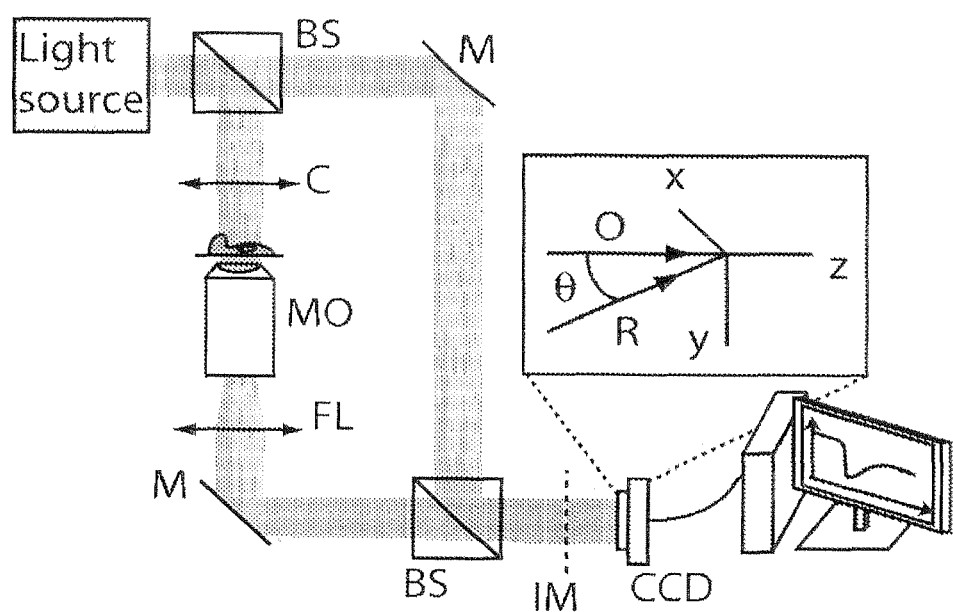
FIG. 3 presents schematically a transmission digital holographic microscope that can be used to measure, in a time resolved way, an optical property for early diagnosis of cell death according to the present invention. BS: beamsplitter, M: Mirror C: Condenser lens, MO: Microscope objective, FL: Field lens, IM: Image plane. A computer analyses the signal detected at the CCD camera to retrieve the optical parameter.

The particular implementation is a transmission DHM setup making possible to monitor cells in time through phase measurement. The sketch of the optical arrangement of the measurement setup is shown in FIG. 3, where the light emitted by a light source is split into two beams and recombined to generate an interference producing a hologram on the camera. This interference occurs between a reference wave that do not interact with the sample, and an object wave collected by a microscope objective (MO) after interaction with the sample. Phase images are reconstructed by a numerical method for off-axis digital hologram reconstruction.

DHM is of particular interest for implementing an apparatus according to the present invention because it enables a fast and easy access to the phase information of the object wave, which is of particular relevance to probe cell regulation processes and to define a variety of phenotype related to morphology, intracellular content or cell membrane properties for example. DHM also enables a fully automated access to the phase information. But it is clear that the present invention is not restricted to the use of a transmission DHM, as described as a pure example in FIG. 3. It is also clear that optical components such as lenses, mirrors, wave-plates and prisms can be added on the general setup of FIG. 3.

In the different experiments described below, the optical property, employed for cell death detection is the mean phase value measured on cell bodies and monitored during time. The phase value is intrinsically a relative measurement that has to be compared with a phase reference, usually taken as the phase shift induced by the perfusion medium. Physically, the phase value $\varphi$ can thus be related to an optical path length (OPL) as $$\varphi_i(x, y) - \varphi_m(x, y) = \Delta\varphi(x, y) = \frac{2\pi}{\lambda}(n_i - n_m)h(x, y), \quad (1)$$

where the indices i and m correspond respectively to the intracellular content of the cell and to the perfusion medium, h is the height of the cell at position (x, y) and n is the mean refractive index (RI) along the optical axis. The phase is measured by calculating a spatial averaging of the phase value on a constant surface contained in the cell body, to which a reference phase value measured on a zone of the field of view containing no biological material has been subtracted.

The meaning of the phase measured with an interferometric method in this context is dependent on the height of the cell and on its intracellular RI. Therefore, the phase is linked both to the cell volume phenotype (through cell height), and to the intracellular content of cells phenotype (through RI), and thus indirectly to the osmotic regulation of the cell. The phase signal is therefore an indicator of cell volume regulation through both parameters, and can be indirectly linked to homeostasis through osmotic phenomena.

This particular study is performed on primary cultures of mouse cortical neurons, mounted on coverslips for optical measurement. Before experiment, coverslips are mounted on a perfusion chamber used to apply the different solutions to the cells, which are immersed in a HEPES-buffered standard physiological perfusion medium. As an example of application of cell death detection through volume regulation, we present in the following a detection of neuronal death induced through glutamate-induced excitotoxic stimulation, ultimately leading to cell death. The glutamate is a neurotransmitter activating neuronal receptors, leading under strong exposure to high level of intracellular calcium concentration, which can lead to death pathway triggering if not regulated properly.

In order to validate the measurement principle proposed in this application, the cell viability is also tested with trypan blue 0.4% reagent, to enable comparative measurements. The dye relies on probing the cell membrane integrity, which becomes permeable to the color compound at a certain level after cell death mechanisms started. After reagent wash-out, the cell nuclei of non-viable cells are consequently stained in blue, as the dye fixes on DNA material. Excitotoxic effects were studied during the experiments, by applying glutamate pulses at different concentration to the cells. The excitation solutions were prepared with concentrations ranging between 25 µM and 100 µM, depending on the type of experiment. Perfusion changes were performed by washing the chamber with a micropipette, making it possible to replace the perfusion medium through typically two washes of the medium.

In order to enable color measurement for cell viability assessment with the reagent, a flip mirror is inserted after the MO, so that the intensity image could also be recorded in focus with a color camera. When performing trypan blue staining, the illumination is changed to employ an incoherent halogen white light source to enable color measurement; this implies that during dye probing, no DHM measurement is performed, yielding part of unmeasured phase signal during time monitoring. Image merging between the two measurement techniques could be done through calibration of the system by imaging an object whose shape is well-known.

To demonstrate the validity of the phenotypic detection approach based on volume regulation, we performed a prolonged application of glutamate at a concentration of 50 µM during 90 seconds. The mean phase value measured on four cell bodies is shown in FIG. 4(a), where the reagent has been applied several times on the culture with an interval of approximately one hour. The phase signals presented correspond to the cells shown in FIG. 4(b). One can identify that among the four curves shown, three present a strong phase signal drop of approximately 40°, while cell 4 retrieves the same mean phase value after a short period of time of approximately 10 minutes, while having phase variations below 10°. The strong phase drops can be interpreted as an irreversible deregulation of the cell volume, which ultimately leads to cell death, while the recovery of the other signal corresponds to a rapid regulation of cell volume.

Figure 4:
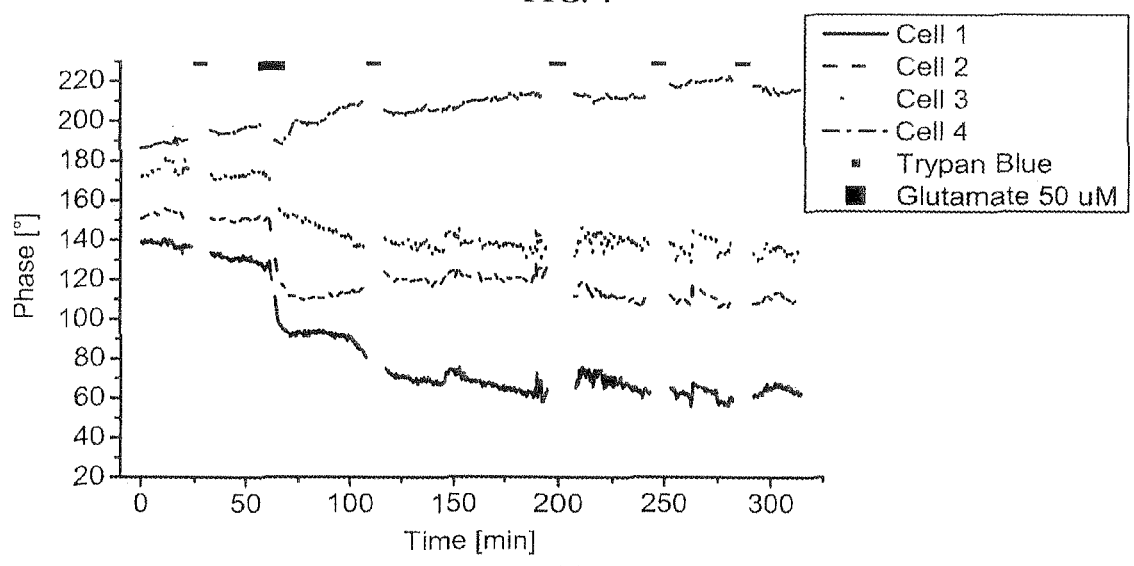
FIG. 4 presents an example of one embodiment of the present invention with a measurement of cell regulation measured through digital holographic microscopy for cell death detection, in order to show the validity of the approach. (a) Curve of the optical phase measured as a function of time, when a drug is employed to induce cell death. In this particular case, cell 4 shows clearly a volume regulation, indicating that this particular cell survived the drug exposure. This behavior has been confirmed with an assessment dye (trypan blue) by (b) first checking cell morphology before the experiment, and then (c) several hours after the experiment, showing that cell 4 is not stained by the dye, while the other dead cells are stained.
Figure 4:
Figure 4:
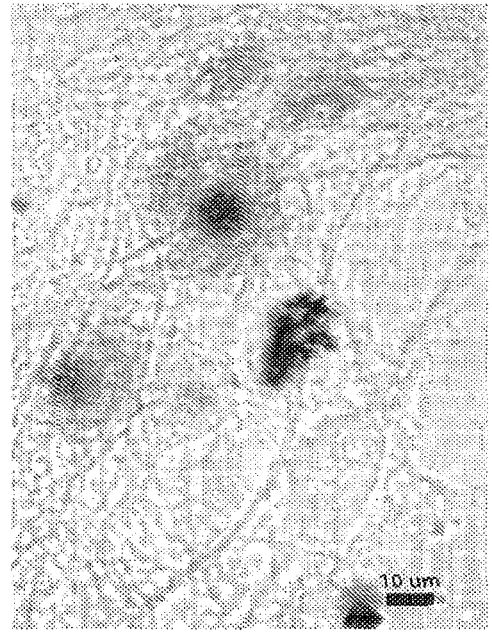

Brightfield color images of the culture, enabling the assessment through the trypan blue dye as a control experiment, are presented in FIGS. 4(b-c), respectively at t=30 min before the excitotoxic stimulation and t=290 min, where non viable cells are identified by the blue staining. The staining confirms the interpretation derived from the phase signal, as the nuclei of cells 1 to 3 were stained at respectively t=116 min, t=207 min and t=252 min, confirming cell death, while cell 4 remained unstained with a healthy morphology, which shows that this cell is still viable several hours after the drug exposure.

Figure 5:
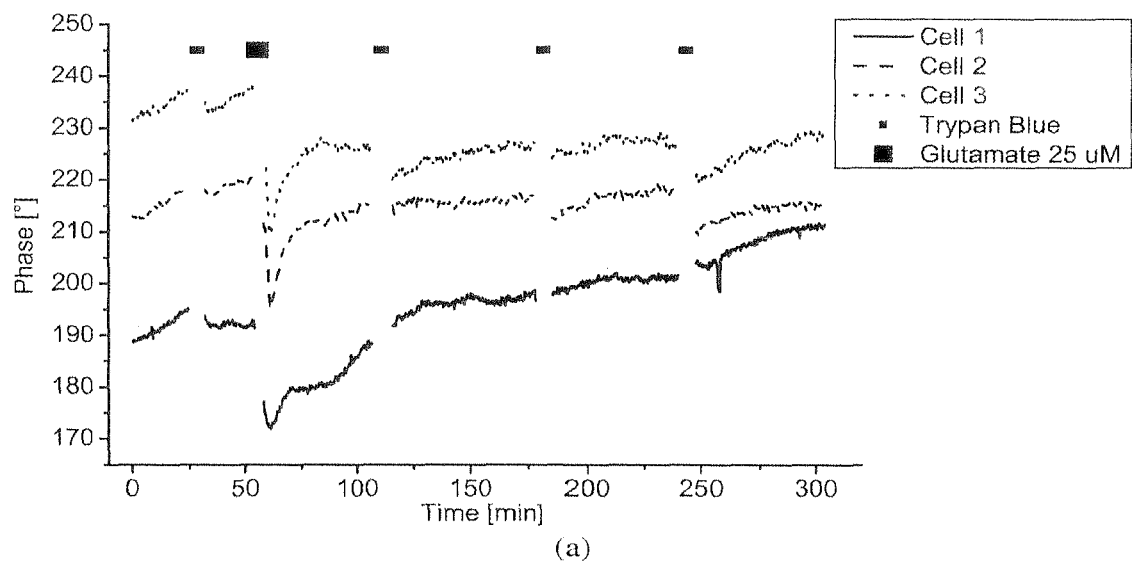
FIG. 5 shows examples of curves of time-resolved phase values measured through digital holographic microscopy, where (a) cells survive the drug exposure, showed through the signal reversibility, or where (b) cells do not survive the drug exposure, as it is indicated by the non-reversibility of the signal.
Figure 5:
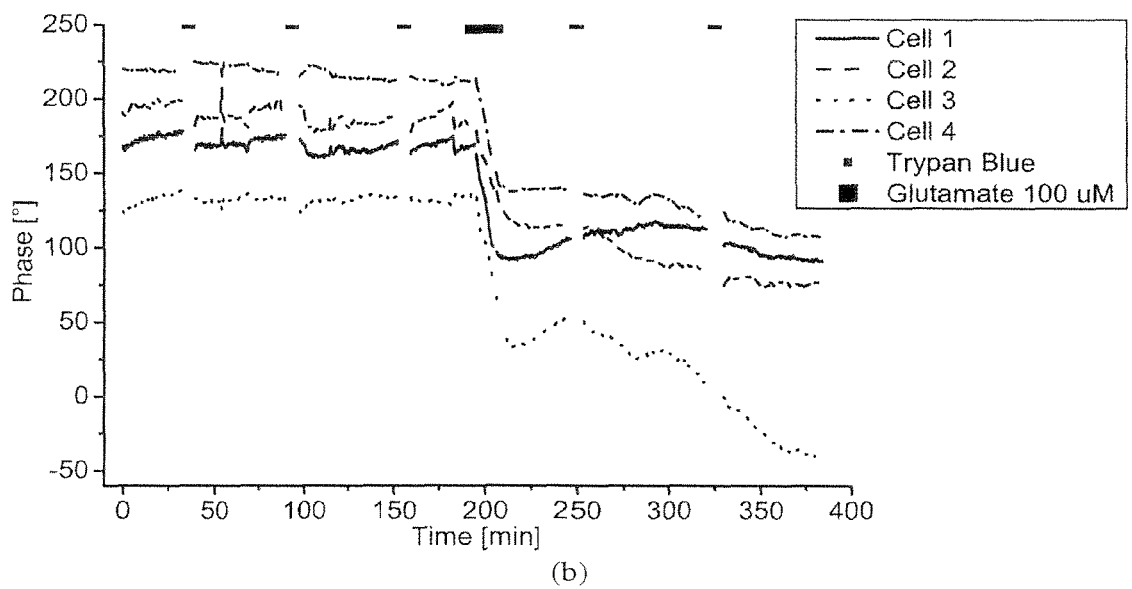

Those results could be reproduced on several cultures, as shown in FIG. 5., where slightly different parameters of stimulations were employed. In FIG. 5(a), a glutamate pulse of 90 seconds (25 µM) produced reversible responses in phase, comparable to the one of cell 4 in the previous experiment. The viability of cells could be confirmed with the reagent up to 4 hours and 30 minutes after stimulation, time at which the experiment was interrupted, with all cells being unstained and having a healthy morphology similar to the one at the beginning of the experiment. In FIG. 5(b), a pulse of 120 seconds (50 µM) produced irreversible phase drops of typically 40° to 50°. In a similar way, cell death could be confirmed with the reagent approximately 4 hours after the stimulation (t=323 min for cells 1 and 2, and t=385 min for cell 3). Curves of both experiments presented in FIG. 5 are representative of measurements on n=10 cells each.

One can identify from the different experiments presented above that signal dynamics for the different concentrations employed for stimulation are fairly comparable and occurring in time frames in order of tens of minutes, time after which a steady-state is reached, either with a strong phase drop, or with a phase value recovery, depending on the viability of the cell considered. Furthermore, it is possible to identify a reproducible behavior regards to excitotoxic stimulation concentrations and durations, as a 50 µM, 90 s pulse generated mixed responses between recovery and death in cultures, a 25 µM, 90 s pulse induced only recovery curves, and 50 µM, 120 s induced irreversible signals. The responses to similar concentrations and durations could be reproduced on several cultures.

The different experiments presented above show a very good agreement between cell viability assessment through dye reagent and volume phenotype monitoring through DHM for cell death detection, although both techniques rely on very different detection methods. On one side, the trypan blue reagent relies on the change of membrane permeability which happens during necrosis, occurring either as the primary cause of cell death mechanism, or as secondary necrosis. The altered permeability of the membrane makes it possible for the dye to penetrate the cell, and therefore stain the nucleus. This implies that both cell and nucleus membranes are altered, classically creating a residual stain in the cell body before staining clearly the nucleus. Many different dyes assessing cell viability rely on the cell membrane permeability as the primary indicator, such as trypan blue or propidium iodide (PI). This type of staining is commonly considered as aspecific, as they are not capable of distinguishing between primary necrosis and apoptosis, during which secondary necrosis occurs at a late stage in cell cultures.

On the other hand, the proposed method example in this feasibility demonstration relies on the dynamic measurement of cell morphology phenotypes, and more specifically cell volume regulation. DHM provides the possibility of measuring dynamically this phenotypic parameter on the whole field of view in real time, making it possible to monitor the cell morphology with a time resolution in milliseconds.

CONCLUSION

Cell volume regulation measurement, and more generally optically-retrieved phenotypes linked to homeostasis provide a simple mean for early and time-effective cell death detection, while cell viability assessment through staining reagents may take up to several hours after the drug application. Employing different phenotypes provided by the DHM measurement or other optical measurement means enables a faster detection. First, one can identify that if cells did not yet regulate regarding its environment during a given time after the drug application, it will not be possible for regulation mechanisms to occur at a sufficient speed to recover from the shock. Furthermore, as exposed for example in the previous feasibility demonstration with the volume phenotype, one can also see that the magnitudes of the phenotype changes are dramatically different for cells regulating, e.g. their volumes, and cells for which death mechanisms were triggered. In the latter case, larger phase changes are occurring, while in the case of cells recovering, phase decrease is finally compensated by the regulation mechanisms, so that small changes only are observed. Those criteria enable an easy diagnostic for cell viability through dynamic measurements of phenotypes, making it possible to define thresholds at which the cell will not recover, and for which cell death mechanisms started.

REFERENCES

Duprez, L. et al. "Major cell death pathways at a glance", *Microbes Infect.* 11(13), 1050-1062 (2009).

Bortner, C. and Cidlowski, J., "The role of apoptotic volume decrease and ionic homeostasis in the activation and repression of apoptosis," *Pflug. Arch. Eur. J. Physiol.* 448(3), 313-318 (2004).

Colomb, T., E. Cuche, N. Aspert, J. Kühn, P. Marquet, C. Depeursinge, F. Montfort, F. Charrière, A. Marian, S. Bourquin et al. *Wave Front Sensing Method And Apparatus*, WO2006090320 (2006).

Cuche, E., and C. Depeursinge. *Method for simultaneous amplitude and quantitative phase contrast imaging by adjusting reconstruction parameters for definition of digital replica of reference wave and aberration parameters correction digitally*, EP1119798 (2000).

P. Marquet, E. Cuche, C. Depeursinge, P. Magistretti, *Apparatus and Method for Digital holographic imaging*, EP1451646 (2003),

The invention claimed is:

1. An apparatus for monitoring cell viability in a sample, said apparatus comprising:
   an emitter for providing an electromagnetic wave for interaction with at least one cell of said sample;
   a measurement device configured to measure at least one optical property of said cell, said at least one optical property being probed with said electromagnetic wave and said at least one optical property being the phase of said electromagnetic wave interacting with said at least one cell; wherein said measurement device comprises
   a digital holographic microscope to make temporally resolved measurements of the phase of said electromagnetic wave interacting with said at least one cell to monitor for a cell mechanism activated to restore a cell homeostatic equilibrium of said at least one cell after a cell environment perturbation; and a processer configured to:
(i) determine a sustained decrease in said temporally resolved measured phase value from an upper phase value of said temporally resolved measured phase value;
(ii) determine an inversion of said sustained decrease and a sustained increase in said temporally resolved measured phase value to a level comparable to said upper phase value, and
(iii) determine that said cell mechanism has been activated to restore a cell homeostatic equilibrium of said at least one cell after a cell environment perturbation and that said at least one cell is viable if said inversion of said sustained decrease and said sustained increase in said temporally resolved measured phase value to a level comparable to said upper phase value are determined.

2. The apparatus according to claim 1, wherein the apparatus is configured to measure from said phase at least one selected from the group consisting of: optical path length of cells, index of refraction of cells, thickness of cells, volume of cells, surface of cells, morphology of cells, protein content of cells, and water concentration of cells.

3. The apparatus according to claim 1, wherein the processor is further configured to determine cell death has occurred if said inversion of said sustained decrease or increase and said sustained increase or decrease in said temporally resolved measured phase value to a level comparable to said upper or lower phase value respectively are not determined.

4. The apparatus according to claim 3, wherein the processor is configured to evaluate from said phase at least one selected from the group consisting of: optical path length of cells, index of refraction of cells, thickness of cells, volume of cells, surface of cells, morphology of cells, protein content of cells, and water concentration of cells.

5. The apparatus according to claim 1, wherein said processor is configured to process the temporally resolved measurements of said optical property to analyze at least one phenotype selected from the group consisting of apoptosis, necrosis, and autophagy.

6. The apparatus according to claim 1, wherein the processor is configured to determine a sustained decrease in said temporally resolved measured phase value to a level comparable to said lower phase value and that differs from said lower phase value by a phase value that is equal or less than a phase value amount corresponding to at least one physiological variation of the at least one cell.

7. An apparatus for monitoring cell viability in a sample, said apparatus comprising:
an emitter for providing an electromagnetic wave for interaction with at least one cell of said sample;
a measurement device configured to measure at least one optical property of said cell, said at least one optical property being probed with said electromagnetic wave and said at least one optical property being the phase of said electromagnetic wave interacting with said at least one cell;
wherein said measurement device comprises at least one device selected from the group consisting of an interferometer, a wavefront sensor, and a phase-contrast microscope to make temporally resolved measurements of the phase of said electromagnetic wave interacting with said at least one cell to monitor for a cell mechanism activated to restore a ell homeostatic equilibrium of said at least one cell after a cell environment perturbation; and a processor configured to:
(i) determine a sustained decrease in said temporally resolved measured phase value from an upper phase value of said temporally resolved measured phase value;
(ii) determine an inversion of said sustained decrease and a sustained increase in said temporally resolved measured phase value to a level comparable to said upper phase value, and
(iii) determine that said cell mechanism has been activated to restore a cell homeostatic equilibrium of said at least one cell after a cell environment perturbation and that said at least one cell is viable if said inversion of said sustained decrease and said sustained increase in said temporally resolved measured phase value to a level comparable to said upper phase value are determined.

8. The apparatus according to claim 7, wherein the apparatus is configured to measure from said phase at least one selected from the group consisting of: optical path length of cells, index of refraction of cells, thickness of cells, volume of cells, surface of cells, morphology of cells, protein content of cells, and water concentration of cells.

9. The apparatus according to claim 7, wherein the processor is further configured to determine cell death has occurred if said inversion of said sustained decrease or increase and said sustained increase or decrease in said temporally resolved measured phase value to a level comparable to said upper or lower phase value respectively are not determined.

10. The apparatus according to claim 9, wherein the processor is configured to evaluate from said phase at least one selected from the group consisting of: optical path length of cells, index of refraction of cells, thickness of cells, volume of cells, surface of cells, morphology of cells, protein content of cells, and water concentration of cells.

11. The apparatus according to claim 7, wherein the processor is configured to process said temporally resolved measurements of said optical property are carried out to analyze at least one phenotype selected from the group consisting of apoptosis, necrosis, and autophagy.

12. The apparatus according to claim 7, wherein the processor is configured to determine a sustained decrease in said temporally resolved measured phase value to a level comparable to said lower phase value and that differs from said lower phase value by a phase value that is equal or less than a phase value amount corresponding to at least one physiological variation of the at least one cell.

13. An apparatus for monitoring cell viability in a sample, said apparatus comprising:
an emitter for providing an electromagnetic wave for interaction with at least one cell of said sample;
a measurement device configured to measure at least one optical property of said cell, said at least one optical property being probed with said electromagnetic wave and said at least one optical property being the phase of said electromagnetic wave interacting with said at least one one cell; wherein said measurement device comprises a digital holographic microscope to make temporally resolved measurements of the phase of said electromagnetic wave interacting with said at least one cell to monitor for a cell mechanism activated to restore a cell homeostatic equilibrium of said at least one cell after a cell environment perturbation; and a processor configured to:
  (i) determine a sustained increase in said temporally resolved measured phase value from a lower phase value of said temporally resolved measured phase value;
  (ii) determine an inversion of said sustained increase and a sustained decrease in said temporally resolved measured phase value to a level comparable to said lower phase value, and
  (iii) determine that said cell mechanism has been activated to restore a cell homeostatic equilibrium of said at least one cell after a cell environment perturbation and that said at least one cell is viable if said inversion of said sustained increase and said sustained decrease in said temporally resolved measured phase value to a level comparable to said lower phase value are determined.

14. The apparatus according to claim 13, wherein the apparatus is configured to measure from said phase at least one selected from the group consisting of: optical path length of cells, index of refraction of cells, thickness of cells, volume of cells, surface of cells, morphology of cells, protein content of cells, and water concentration of cells.

15. The apparatus according to claim 13, wherein the processor is further configured to determine cell death has occurred if said inversion of said sustained decrease or increase and said sustained increase or decrease in said temporally resolved measured phase value to a level comparable to said upper or lower phase value respectively are not determined.

16. The apparatus according to claim 15, wherein the processor is configured to evaluate from said phase at least one selected from the group consisting of: optical path length of cells, index of refraction of cells, thickness of cells, volume of cells, surface of cells, morphology of cells, protein content of cells, and water concentration of cells.

17. The apparatus according to claim 13, wherein said processor is configured to process the temporally resolved measurements of said optical property to analyze at least one phenotype selected from the group consisting of apoptosis, necrosis, and autophagy.

18. The apparatus according to claim 13, wherein the processor is configured to determine a sustained increase in said temporally resolved measured phase value to a level comparable to said upper phase value and that differs from said upper phase value by a phase value that is equal or less than a phase value amount corresponding to at least one physiological variation of the at least one cell.

19. An apparatus for monitoring cell viability in a sample, said apparatus comprising:
  an emitter for providing an electromagnetic wave for interaction with at least one cell of said sample;
  a measurement device configured to measure at least one optical property of said cell, said at least one optical property being probed with said electromagnetic wave and said at least one optical property being the phase of said electromagnetic wave interacting with said at least one cell;
  wherein said measurement device comprises at least one device selected from the group consisting of an interferometer, a wavefront sensor, and a phase-contrast microscope to make temporally resolved measurements of the phase of said electromagnetic wave interacting with said at least one cell to monitor for a cell mechanism activated to restore a cell homeostatic equilibrium of said at least one cell after a cell environment perturbation; and
  a processor configured to:
    (i) determine a sustained increase in said temporally resolved measured phase value from a lower phase value of said temporally resolved measured phase value;
    (ii) determine an inversion of said sustained increase and a sustained decrease in said temporally resolved measured phase value to a level comparable to said lower phase value, and
    (iii) determine that said cell mechanism has been activated to restore a cell homeostatic equilibrium of said at least one cell after a cell environment perturbation and that said at least one cell is viable if said inversion of said sustained increase and said sustained decrease in said temporally resolved measured phase value to a level comparable to said lower phase value are determined.

20. The apparatus according to claim 19, wherein the apparatus is configured to measure from said phase at least one selected from the group consisting of: optical path length of cells, index of refraction of cells, thickness of cells, volume of cells, surface of cells, morphology of cells, protein content of cells, and water concentration of cells.

21. The apparatus according to claim 19, wherein the processor is further configured to determine cell death has occurred if said inversion of said sustained decrease or increase and said sustained increase or decrease in said temporally resolved measured phase value to a level comparable to said upper or lower phase value respectively are not determined.

22. The apparatus according to claim 21, wherein the processor is configured to evaluate from said phase at least one selected from the group consisting of: optical path length of cells, index of refraction of cells, thickness of cells, volume of cells, surface of cells, morphology of cells, protein content of cells, and water concentration of cells.

23. The apparatus according to claim 19, wherein the processor is configured to process said temporally resolved measurements of said optical property are carried out to analyze at least one phenotype selected from the group consisting of apoptosis, necrosis, and autophagy.

24. The apparatus according to claim 19, wherein the processor is configured to determine a sustained increase in said temporally resolved measured phase value to a level comparable to said upper phase value and that differs from said upper phase value by a phase value that is equal or less than a phase value amount corresponding to at least one physiological variation of the at least one cell.

* * * * *